(12) United States Patent
Hudon et al.

(10) Patent No.: US 12,116,630 B2
(45) Date of Patent: Oct. 15, 2024

(54) METHODS AND COMPOSITIONS FOR ASSAYING REPETITIVE SEQUENCES

(71) Applicant: Boise State University, Boise, ID (US)

(72) Inventors: Stephanie F. Hudon, Boise, ID (US); Steven Burden, Boise, ID (US); Eric Hayden, Boise, ID (US); Esteban Palencia Hurtado, Hailey, ID (US)

(73) Assignee: Boise State University, Boise, ID (US)

( * ) Notice: Subject to any disclaimer, the term of this patent is extended or adjusted under 35 U.S.C. 154(b) by 767 days.

(21) Appl. No.: 16/948,526

(22) Filed: Sep. 22, 2020

(65) Prior Publication Data

US 2021/0087628 A1 Mar. 25, 2021

Related U.S. Application Data

(60) Provisional application No. 62/904,422, filed on Sep. 23, 2019.

(51) Int. Cl.
*C12Q 1/68* (2018.01)
*C12Q 1/6876* (2018.01)

(52) U.S. Cl.
CPC ..... *C12Q 1/6876* (2013.01); *C12Q 2600/124* (2013.01); *C12Q 2600/166* (2013.01)

(58) Field of Classification Search
None
See application file for complete search history.

(56) References Cited

U.S. PATENT DOCUMENTS

| | | | |
|---|---|---|---|
| 9,169,516 B2 | 10/2015 | Cawthon | |
| 10,093,970 B2 | 10/2018 | Keefe et al. | |
| 10,407,739 B2 | 9/2019 | Nair et al. | |
| 2016/0032360 A1* | 2/2016 | Keefe | C12Q 1/6876 435/6.12 |
| 2019/0338355 A1 | 11/2019 | Frasch et al. | |

OTHER PUBLICATIONS

Asghar et al., "Are chronic avian haemosporidian infections costly in wild birds?", J. Avian Biol., vol. 42, pp. 530-537, Apr. 7, 2011.

* cited by examiner

*Primary Examiner* — Jehanne S Sitton
(74) *Attorney, Agent, or Firm* — McKee, Voorhees & Sease, PLC

(57) ABSTRACT

Disclosed herein are methods of determining telomere length using universal reference primers. The reference primer pairs efficiently and reproducibly amplify genomic DNA in any vertebrate species. Kits for determining the length of telomeres or others repetitive regions in a sample are also provided.

12 Claims, 12 Drawing Sheets
(7 of 12 Drawing Sheet(s) Filed in Color)
Specification includes a Sequence Listing.

| UCE | Efficiency | $R^2$ |
|---|---|---|
| UCE.359 | 97% | 0.99 |
| UCE.28 | 95% | 0.99 |
| UCE.64 | 101% | 0.99 |
| UCE.239 | 101% | 0.99 |
| UCE.176 | 102% | 0.99 |

FIG. 1C

SEQUENCE LISTING

<160> NUMBER OF SEQ ID NOS: 14

<210> SEQ ID NO 1
<211> LENGTH: 18
<212> TYPE: DNA
<213> ORGANISM: Artificial Sequence
<220> FEATURE:
<223> OTHER INFORMATION: Primer

<400> SEQUENCE: 1
atctgagact tgtgacat                                        18

<210> SEQ ID NO 2
<211> LENGTH: 22
<212> TYPE: DNA
<213> ORGANISM: Artificial Sequence
<220> FEATURE:
<223> OTHER INFORMATION: Primer

<400> SEQUENCE: 2

```
gtgttaattg gtaatgacta tt                                              22

<210> SEQ ID NO 3
<211> LENGTH: 19
<212> TYPE: DNA
<213> ORGANISM: Artificial Sequence
<220> FEATURE:
<223> OTHER INFORMATION: Primer

<400> SEQUENCE: 3
aaataccacc caacagttt                                                  19

<210> SEQ ID NO 4
<211> LENGTH: 19
<212> TYPE: DNA
<213> ORGANISM: Artificial Sequence
<220> FEATURE:
<223> OTHER INFORMATION: Primer

<400> SEQUENCE: 4
aagccctata cagatggat                                                  19

<210> SEQ ID NO 5
<211> LENGTH: 23
<212> TYPE: DNA
<213> ORGANISM: Artificial Sequence
<220> FEATURE:
<223> OTHER INFORMATION: Primer

<400> SEQUENCE: 5
gagtctccaa tatcatcaga agc                                             23

<210> SEQ ID NO 6
<211> LENGTH: 19
<212> TYPE: DNA
<213> ORGANISM: Artificial Sequence
<220> FEATURE:
<223> OTHER INFORMATION: Primer

<400> SEQUENCE: 6
acacatgcca cgatcaatg                                                  19

<210> SEQ ID NO 7
<211> LENGTH: 18
<212> TYPE: DNA
<213> ORGANISM: Artificial Sequence
<220> FEATURE:
<223> OTHER INFORMATION: Primer

<400> SEQUENCE: 7
tcagatgttc agcctatt                                                   18

<210> SEQ ID NO 8
<211> LENGTH: 23
<212> TYPE: DNA
<213> ORGANISM: Artificial Sequence
<220> FEATURE:
<223> OTHER INFORMATION: Primer

<400> SEQUENCE: 8
aataccatgt taattatcct caa                                             23

<210> SEQ ID NO 9
<211> LENGTH: 24
<212> TYPE: DNA
<213> ORGANISM: Artificial Sequence
```

```
<220> FEATURE:
<223> OTHER INFORMATION: Primer

<400> SEQUENCE: 9
tttctacagt tctgatttag ttga                                          24

<210> SEQ ID NO 10
<211> LENGTH: 18
<212> TYPE: DNA
<213> ORGANISM: Artificial Sequence
<220> FEATURE:
<223> OTHER INFORMATION: Primer

<400> SEQUENCE: 10
tgttccctgt cgcattag                                                 18

<210> SEQ ID NO 11
<211> LENGTH: 39
<212> TYPE: DNA
<213> ORGANISM: Artificial Sequence
<220> FEATURE:
<223> OTHER INFORMATION: Primer

<400> SEQUENCE: 11
cggtttgttt gggtttgggt tgggtttgg gtttgggtt                           39

<210> SEQ ID NO 12
<211> LENGTH: 45
<212> TYPE: DNA
<213> ORGANISM: Artificial Sequence
<220> FEATURE:
<223> OTHER INFORMATION: Primer

<400> SEQUENCE: 12
cagccgaaag gcccttggca ggagggctgc tggtggtcta ccctt                   45

<210> SEQ ID NO 13
<211> LENGTH: 18
<212> TYPE: DNA
<213> ORGANISM: Artificial Sequence
<220> FEATURE:
<223> OTHER INFORMATION: Primer

<400> SEQUENCE: 13
ctaagcgtgt tatcatct                                                 18

<210> SEQ ID NO 14
<211> LENGTH: 18
<212> TYPE: DNA
<213> ORGANISM: Artificial Sequence
<220> FEATURE:
<223> OTHER INFORMATION: Primer

<400> SEQUENCE: 14
acttgtcata cttgtcat                                                 18
```

METHODS AND COMPOSITIONS FOR ASSAYING REPETITIVE SEQUENCES

CROSS-REFERENCE TO RELATED APPLICATIONS

This application claims priority to provisional application U.S. Ser. No. 62/904,422, filed Sep. 23, 2019, which is incorporated herein by reference in its entirety.

SEQUENCE LISTING

The instant application contains a Sequence Listing which has been submitted in ASCII format via EFS-Web and is hereby incorporated by reference in its entirety. Said ASCII copy, created on Sep. 14, 2020, is named 2020-09-22_HUDON_P13012US01_SEQLISTING_ST25.txt and is 2,854 bytes in size.

FIELD OF THE INVENTION

The present disclosure relates to nucleic acid sequences and methods of using the same for determining the length of telomeres or other repetitive regions. Kits for amplifying a reference sequence and determining telomere length are also provided.

BACKGROUND OF THE INVENTION

The measurement of telomere lengths is an important approach used to study the health and aging of organisms. Telomeres are structures at the end of eukaryotic chromosomes that are comprised of proteins bound to repetitive DNA sequences. Telomeres protect the ends of linear chromosomes and provide several important cellular functions. The length of telomere DNA shortens at each cell division, and telomere shortening can eventually lead to cellular senescence, which affects tissue function, organismal health and lifespan. Telomere lengths are considered an indicator of phenotypic quality and telomere length dynamics have been shown to have predictive power of the future success of organisms. For example, telomere shortening has been shown to predict both lifespan and reproductive success, which are proxies for organismal fitness. Short telomere lengths have even been suggested to precede extinction events. In addition, telomere shortening has been shown to be accelerated by various forms of stress and telomere lengths have been used to evaluate environmental quality. The ability to monitor the well-being of organisms and to predict their future success has important applications in both wild and captive environments. In addition, understanding telomere dynamics across the vertebrate tree of life could also lead to a better understanding of the mechanisms and evolution of aging in general.

Despite the motivation for measuring telomere lengths, research remains limited to relatively few species, with the majority of studies done in avian species. Methodological challenges are one reason for the limited use of telomere length measurements. A widely used method is to measure relative telomere length by real-time quantitative PCR (qPCR). This method requires only common lab equipment and techniques, can be done in relatively high-throughput and is robust despite low sample quantity and quality. Measurement of telomere length by qPCR requires primers that amplify telomere repeats, where the concentration of telomeric DNA in a sample, determined by qPCR, is proportional to telomere length. The method also requires reference primers that amplify a non-telomeric region of the genome of interest to normalize for the total amount of genomic DNA in the sample. The repeating DNA sequence of telomeres (TTAGGG) is identical in all vertebrates, so the established telomere-specific primer pairs should work in any vertebrate species. In contrast, the genome specific reference primers optimized in one species may not work in other species because of unknown genetic differences, often requiring the design and optimization of new primers for each new species that is to be studied. Reference primer development is especially challenging in non-model organisms with genomes that have not been sequenced. Despite the wide potential application of measuring telomere lengths by qPCR, reference primer design may limit the adoption of this assay in newly analyzed species.

SUMMARY OF THE INVENTION

The present disclosure provides reference oligonucleotide pairs that can be used in any vertebrate species including use in qPCR to measure length of telomeres or other repetitive regions as well as other methods requiring quantification of genomic DNA. The pairs amplify genetic elements that are highly conserved between evolutionarily distant taxa and meet the specificity and reproducibility standards of qPCR. These reference oligonucleotide pairs can facilitate qPCR-based telomere length measurements in any vertebrate species of ecological or economic interest. Described herein are methods, compositions, and kits directed to the reference oligonucleotide pairs.

In one aspect, methods for determining telomere length in a genomic DNA sample are provided. The methods comprise amplifying the genomic DNA with a first oligonucleotide pair specific for a telomere repeat and a second oligonucleotide pair specific for a reference sequence. The second oligonucleotide pair specific for the reference sequence comprises SEQ ID NOs: 1 and 2, SEQ ID NOs: 3 and 4, SEQ ID NOs: 5 and 6, SEQ ID NOs: 7 and 8, or SEQ ID NOs: 9 and 10 or portions thereof. In an embodiment, the sequences are 3, 4, 5, 6, 7, 8, 9, 10, 11, 12, 13, 14, 15, 16, 17, 18, 19, 20, 21, 22, 23, 24, 25, 26, 27, 28, 29, 30, 31 32, 33, 34, or 35 contiguous bases thereof including conservatively modified variants of either that specifically bind and target the desired reference sequence. In one embodiment, the first oligonucleotide pair specific for a telomere repeat comprises SEQ ID NOs: 11 and 12 or a portion thereof that will hybridize with the desired site. In one embodiment, telomere length is used to predict the lifespan or reproductive success of an organism. In another embodiment, telomere length is used to determine the age of a cell.

In some embodiments, the amplifying is performed using quantitative RT-PCR. The amount of amplification product produced by the first oligonucleotide pair is normalized to the amount of amplification product produced by the second oligonucleotide pair to determine the length of the repetitive region. In one embodiment, at least one oligonucleotide of each oligonucleotide pair is associated with a detectable label. In some embodiments, the oligonucleotide pairs are contained together in an amplification master mix further comprising DNA polymerase, dNTPs, and PCR buffer prior to contacting with the sample and amplifying the target nucleic acid. The sample may be from any animal. In some embodiments, the sample is from a chordate including, for example, a mammal, fish, bird, reptile, or amphibian. In one embodiment, the sample is from a human.

In some embodiments, the method comprises amplifying the nucleic acid with two or more reference oligonucleotide pairs selected from SEQ ID NOs: 1 and 2, SEQ ID NOs: 3 and 4, SEQ ID NOs: 5 and 6, SEQ ID NOs: 7 and 8, and SEQ ID NOs: 9 and 10 or portions thereof including conservatively modified variants thereof which will hybridize to the target site and amplify the desired region. Relative telomere length may be calculated as the ratio of the telomere repeat amplification product to the average of the two or more reference amplification products.

In another aspect, kits comprising one or more oligonucleotide pairs capable of amplifying a reference sequence are provided. The one or more oligonucleotide pairs comprise SEQ ID NOs: 1 and 2, SEQ ID NOs: 3 and 4, SEQ ID NOs: 5 and 6, SEQ ID NOs: 7 and 8, or SEQ ID NOs: 9 and 10 or portions thereof including conservatively modified variants thereof which will hybridize to the target site and amplify the desired region. The kits may be for quantifying genomic DNA, determining the length of a repetitive region, determining telomere length, or determining copy number variation of a target sequence. In some embodiments, the kit further comprises an amplification mixture including DNA polymerase, dNTPs, and PCR buffer. Preferably, at least one oligonucleotide of each oligonucleotide pair is associated with a detectable label. The kit may include two, three, four, or all five of the oligonucleotide pairs selected from SEQ ID NOs: 1 and 2, SEQ ID NOs: 3 and 4, SEQ ID NOs: 5 and 6, SEQ ID NOs: 7 and 8, and SEQ ID NOs: 9 and 10, or portions thereof including conservatively modified variants thereof which will hybridize to the target site and amplify the desired region.

While multiple embodiments are disclosed, still other embodiments of the present invention will become apparent to those skilled in the art from the following detailed description, which shows and describes illustrative embodiments of the invention. Accordingly, the figures and detailed description are to be regarded as illustrative in nature and not restrictive.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The following drawings form part of the specification and are included to further demonstrate certain embodiments or various aspects of the invention. In some instances, embodiments of the invention can be best understood by referring to the accompanying drawings in combination with the detailed description presented herein. The description and accompanying drawings may highlight a certain specific example, or a certain aspect of the invention. However, one skilled in the art will understand that portions of the example or aspect may be used in combination with other examples or aspects of the invention.

FIGS. 1A-C show UCE primer performance in mouse. FIG. 1A is a conceptual diagram of the vertebrate telomere assay design. Black bars represent the level of conservation of genomic regions determined by the alignment of multiple genomes such as a bird, a mammal and a fish. Telomeric repeats are conserved in all chordates and are amplified by primers specific to this sequence. The same reference primers can be used in all species because they amplify ultra-conserved elements (UCE) that have high conservation between distant taxa. FIG. 1B shows melt curves of the amplification product of the qPCR of genomic mouse DNA using the best primer pair for each UCE. FIG. 1C shows efficiencies and $R^2$ values of the best primer pair identified for five different UCEs, named by their access number in the UCE database.

FIG. 2A is a phylogenetic tree of organisms in which reference primers were validated (timetree.org). FIG. 2B shows average stability values (pairwise variation) generated in geNorm from the utilization of six to two reference gene primers. FIG. 2C shows Pearson correlation between the genomic DNA concentrations (ng) of the two UCE primer pairs that resulted in the lowest average stability values (geNorm) in each of four organisms. FIG. 2D shows relative telomere length for adult and nestling American kestrels using UCE primers.

FIG. 3A shows goshawk. FIG. 3B shows ptarmigan. FIG. 3C shows mouse. FIG. 3D shows bighorn sheep.

DETAILED DESCRIPTION OF THE INVENTION

Figure 1A:
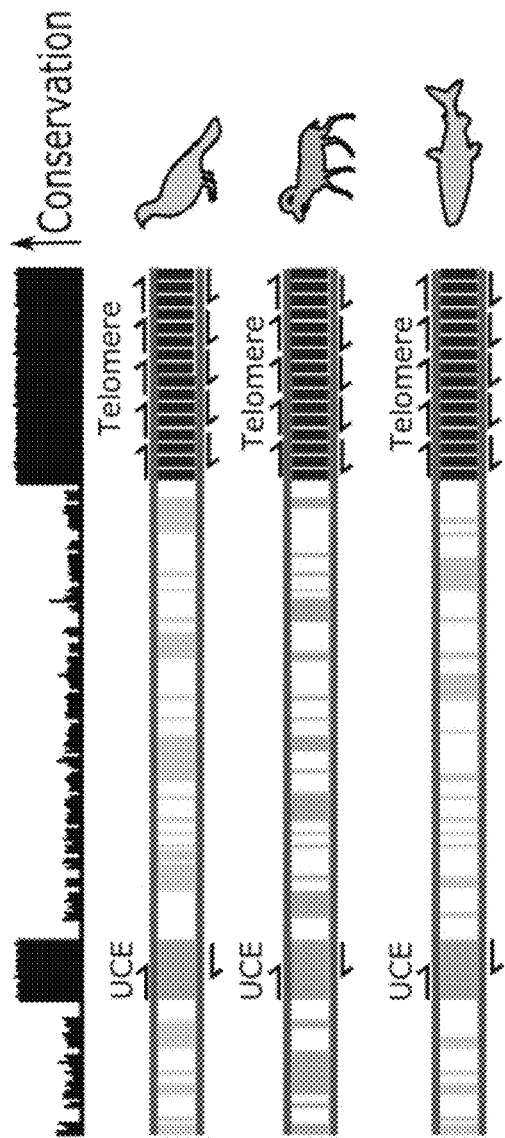

The present invention provides PCR primers that can be used as genomic reference primers in any vertebrate species, including for qPCR based-telomere length measurements. The primers amplify genetic elements that are highly conserved between evolutionarily distant taxa. The primer pairs amplify five different UCEs and also meet qPCR requirements for specificity and efficiency. All five primer pairs efficiently and reproducibly amplify genomic DNA in every vertebrate sample tested. In addition, the targeted UCEs do not vary in copy number in the species investigated.

So that the present invention may be more readily understood, certain terms are first defined. Unless defined otherwise, all technical and scientific terms used herein have the same meaning as commonly understood by one of ordinary skill in the art to which embodiments of the invention pertain. Many methods and materials similar, modified, or equivalent to those described herein can be used in the practice of the embodiments of the present invention without undue experimentation, the preferred materials and methods are described herein. In describing and claiming the embodiments of the present invention, the following terminology will be used in accordance with the definitions set out below.

The singular terms "a", "an", and "the" include plural referents unless context clearly indicates otherwise. Similarly, the word "or" is intended to include "and" unless the context clearly indicates otherwise. The word "or" means any one member of a particular list and also includes any combination of members of that list.

The terms "amplification" or "amplify" as used herein include methods for copying a target nucleic acid, thereby increasing the number of copies of a selected nucleic acid sequence. Amplification may be exponential or linear. A target nucleic acid may be DNA (such as, for example, genomic DNA and cDNA) or RNA. The sequences amplified in this manner form an "amplicon." While the exemplary methods described hereinafter relate to amplification using the polymerase chain reaction (PCR), numerous other methods are known in the art for amplification of nucleic acids (e.g., isothermal methods, rolling circle methods, etc.).

The skilled artisan will understand that these other methods may be used either in place of, or together with, PCR methods. See, e.g., Saiki, "Amplification of Genomic DNA" in PCR Protocols, Innis et al., Eds., Academic Press, San Diego, Calif. 1990, pp 13-20; Wharam, et al., Nucleic Acids Res. 2001 Jun. 1; 29(11):E54-E54; Hafner, et al., Biotechniques 2001 April; 30(4):852-860.

The terms "complement," "complementary," or "complementarity" as used herein with reference to polynucleotides (i.e., a sequence of nucleotides such as an oligonucleotide or a target nucleic acid) refer to standard Watson/Crick pairing rules. The complement of a nucleic acid sequence such that the 5' end of one sequence is paired with the 3' end of the other, is in "antiparallel association." For example, the sequence "5'-A-G-T-3" is complementary to the sequence "3'-T-C-A-S'." Certain bases not commonly found in natural nucleic acids may be included in the nucleic acids described herein; these include, for example, inosine, 7-deazaguanine, Locked Nucleic Acids (LNA), and Peptide Nucleic Acids (PNA). Complementarity need not be perfect; stable duplexes may contain mismatched base pairs, degenerative, or unmatched bases. Those skilled in the art of nucleic acid technology can determine duplex stability empirically considering a number of variables including, for example, the length of the oligonucleotide, base composition and sequence of the oligonucleotide, ionic strength and incidence of mismatched base pairs. A complement sequence can also be a sequence of RNA complementary to the DNA sequence or its complement sequence, and can also be a cDNA. The term "substantially complementary" as used herein means that two sequences specifically hybridize (defined below). The skilled artisan will understand that substantially complementary sequences need not hybridize along their entire length. A nucleic acid that is the "full complement" or that is "fully complementary" to a reference sequence consists of a nucleotide sequence that is 100% complementary (under Watson/Crick pairing rules) to the reference sequence along the entire length of the nucleic acid that is the full complement. A full complement contains no mismatches to the reference sequence.

The term "detectable label" as used herein refers to a molecule or a compound or a group of molecules or a group of compounds associated with a primer or a probe and is used to identify the primer or probe hybridized to a genomic nucleic acid or reference nucleic acid. In some cases, the detectable label may be detected directly. In other cases, the detectable label may be a part of a binding pair, which can then be subsequently detected. Signals from the detectable label may be detected by various means and will depend on the nature of the detectable label. Examples of means to detect detectable label include but are not limited to spectroscopic, photochemical, biochemical, immunochemical, electromagnetic, radiochemical, or chemical means, such as fluorescence, chemifluorescence, or chemiluminescence, or any other appropriate means.

"Genomic nucleic acid" or "genomic DNA" refers to some or all of the DNA from a chromosome. Genomic DNA may be intact or fragmented (e.g. digested with restriction endonucleases by methods known in the art). Methods of purifying DNA and/or RNA from a variety of samples are well-known in the art.

The term "multiplex PCR" as used herein refers to an assay that provides for simultaneous amplification and detection of two or more products within the same reaction vessel. Each product is primed using a distinct primer pair. A multiplex reaction may further include specific probes for each product that are detectably labeled with different detectable moieties.

As used herein, the term "oligonucleotide" refers to a short polymer composed of deoxyribonucleotides, ribonucleotides or any combination thereof. Oligonucleotides are generally at least about 10, 11, 12, 13, 14, 15, 20, 25, 40 or 50 up to about 100, 110, 150 or 200 nucleotides (nt) in length, more preferably from about 10, 11, 12, 13, 14, or 15 up to about 70 or 85 nt, and most preferably from about 15 up to about 26 nt in length. The single letter code for nucleotides is as described in the U.S. Patent Office Manual of Patent Examining Procedure, section 2422, table 1. In this regard, the nucleotide designation "R" means purine such as guanine or adenine, "Y" means pyrimidine such as cytosine or thymidine (uracil if RNA); and "M" means adenine or cytosine. An oligonucleotide may be used as a primer or as a probe.

As used herein, a "primer" for amplification is an oligonucleotide that is complementary to a target nucleotide sequence and leads to addition of nucleotides to the 3' end of the primer in the presence of a DNA or RNA polymerase. The 3' nucleotide of the primer should generally be identical to the target nucleic acid sequence at a corresponding nucleotide position for optimal expression and amplification. The term "primer" as used herein includes all forms of primers that may be synthesized including peptide nucleic acid primers, locked nucleic acid primers, phosphorothioate modified primers, labeled primers, and the like. As used herein, a "forward primer" is a primer that is complementary to the anti-sense strand of dsDNA. A "reverse primer" is complementary to the sense-strand of dsDNA. An "exogenous primer" refers specifically to an oligonucleotide that is added to a reaction vessel containing the sample nucleic acid to be amplified from outside the vessel and is not produced from amplification in the reaction vessel. A primer that is "associated with" a fluorophore or other label is connected to label through some means. An example is a primer-probe.

Primers are typically from at least 3, 4, 5, 10, 15, 18, or 30 nucleotides in length up to about 100, 110, 125, or 200 nucleotides in length, preferably from at least 15 up to about 60 nucleotides in length, and most preferably from at least 25 up to about 40 nucleotides in length. In some embodiments, primers and/or probes are 15 to 35 nucleotides in length. There is no standard length for optimal hybridization or polymerase chain reaction amplification. An optimal length for a particular primer application may be readily determined in the manner described in H. Erlich, PCR Technology, Principles and Application for DNA Amplification, (1989).

A "primer pair" is a pair of nucleic acid sequences that are both directed to target nucleic acid sequence. A nucleic acid sequence pair contains a forward primer and a reverse primer, each of which hybridizes under stringent condition to a different strand of a double-stranded target nucleic acid sequence. The forward sequence is complementary to the anti-sense strand of the dsDNA and the reverse sequence is complementary to the sense-strand. One primer of a primer pair may be a primer-probe (i.e., a bi-functional molecule that contains a PCR primer element covalently linked by a polymerase-blocking group to a probe element and, in addition, may contain a fluorophore that interacts with a quencher).

An oligonucleotide (e.g., a probe or a primer) that is specific for a target nucleic acid will "hybridize" to the target nucleic acid under specified conditions. As used herein, "hybridization" or "hybridizing" refers to the process by which an oligonucleotide single strand anneals with a complementary strand through base pairing under defined hybridization conditions.

"Specific hybridization" is an indication that two nucleic acid sequences share a high degree of complementarity. Specific hybridization complexes form under permissive annealing conditions and remain hybridized after any subsequent washing steps. Permissive conditions for annealing of nucleic acid sequences are routinely determinable by one of ordinary skill in the art and may occur, for example, at 65° C. in the presence of about 6×SSC. Stringency of hybridization may be expressed, in part, with reference to the temperature under which the wash steps are carried out. Such temperatures are typically selected to be about 5° C. to 20° C. lower than the thermal melting point (Tm) for the specific sequence at a defined ionic strength and pH. The Tm is the temperature (under defined ionic strength and pH) at which 50% of the target nucleic acid hybridizes to a perfectly matched probe. Equations for calculating Tm and conditions for nucleic acid hybridization are known in the art. Specific hybridization preferably occurs under stringent conditions, which are well known in the art. Stringent hybridization conditions are hybridization in 50% formamide, 1 M NaCl, 1% SDS at 37° C., and a wash in 0.1×SSC at 60° C. Hybridization procedures are well known in the art and are described in e.g. Ausubel et al, Current Protocols in Molecular Biology, John Wiley & Sons Inc., 1994.

As used herein, an oligonucleotide is "specific" for a nucleic acid if the oligonucleotide has at least 50% sequence identity with the nucleic acid when the oligonucleotide and the nucleic acid are aligned. An oligonucleotide that is specific for a nucleic acid is one that, under the appropriate hybridization or washing conditions, is capable of hybridizing to the target of interest and not substantially hybridizing to nucleic acids which are not of interest. Higher levels of sequence identity are preferred and include at least 75%, at least 80%, at least 85%, at least 90%, at least 95% and more preferably at least 98% sequence identity. Sequence identity can be determined using a commercially available computer program with a default setting that employs algorithms well known in the art. As used herein, sequences that have "high sequence identity" have identical nucleotides at least at about 50% of aligned nucleotide positions, preferably at least at about 60% of aligned nucleotide positions, and more preferably at least at about 75% of aligned nucleotide positions.

Oligonucleotides used as primers or probes for specifically amplifying (i.e., amplifying a particular target nucleic acid) or specifically detecting (i.e., detecting a particular target nucleic acid sequence) a target nucleic acid generally are capable of specifically hybridizing to the target nucleic acid under stringent conditions.

As used herein, "conservatively modified variant" refers to nucleotide sequences containing individual substitutions, deletions, or additions that alter, add or delete a single nucleotide or a small percentage of nucleotides in the sequence, where the nucleotide sequence is sufficiently complementary to hybridize with a template. For example, a primer sequence need not reflect the exact sequence of the template. A non-complementary nucleotide fragment may be attached to the 5' end of the primer, with the remainder of the primer sequence being complementary to the strand. Alternatively, non-complementary bases or longer sequences can be interspersed into the primer, provided that the primer sequence has sufficient complementarity with the sequence of the strand to hybridize therewith and thereby form the template for the synthesis of the extension product.

The term "sample" as used herein refers to a sample which contains nucleic acid or is suspected of containing nucleic acid. In some embodiments, the nucleic acids in the sample are for use in accordance with the methods disclosed herein. In some embodiments, a sample is a biological sample. The term "biological sample" as used herein refers to a sample, which contains target nucleic acids or be used as a source of target nucleic acids for the methods of the invention. In some embodiments, a sample is obtained from a tissue or bodily fluid collected from a subject.

The term "chordate" as used herein refers to an animal of the phylum Chordata, comprising the vertebrates together with the sea squirts and lancelets.

An "amplification mixture" as used herein is a mixture of reagents that are used in a nucleic acid amplification reaction, but does not contain primers or sample. An amplification mixture comprises a buffer, dNTPs, and a DNA polymerase. An amplification mixture may further comprise at least one of $MgCl_2$, KCl, nonionic and ionic detergents (including cationic detergents).

An "amplification master mix" comprises an amplification mixture and primers for amplifying a target nucleic acid, but does not contain a sample to be amplified.

A "reaction-sample mixture" as used herein refers to a mixture containing amplification master mix plus sample.

The terms "target nucleic acid" "target nucleic acid sequence" or "target sequence" as used herein refer to a sequence which includes a segment of nucleotides of interest to be amplified and detected. Copies of the target sequence which are generated during the amplification reaction are referred to as amplification products, amplimers, or amplicons. Target nucleic acid may be composed of segments of a chromosome, a complete gene with or without intergenic sequence, segments or portions of a gene with or without intergenic sequence, or sequence of nucleic acids which probes or primers are designed. Target nucleic acids may include a wild-type sequence(s), a mutation, deletion or duplication, tandem repeat regions, a telomere repeat, a gene of interest, a region of a gene of interest or any upstream or downstream region thereof. Target nucleic acids may represent alternative sequences or alleles of a particular gene. Target nucleic acids may be derived from genomic DNA, cDNA, or RNA. As used herein target nucleic acid may be DNA or RNA extracted from a cell or a nucleic acid copied or amplified therefrom, or may include extracted nucleic acids further converted using a bisulfite reaction.

Nucleic acid samples or target nucleic acids may be amplified by various methods known to the skilled artisan. Preferably, PCR is used to amplify nucleic acids of interest. Briefly, in PCR, two primer sequences are prepared that are complementary to regions on opposite complementary strands of the marker sequence. An excess of deoxynucleotide triphosphates are added to a reaction mixture along with a DNA polymerase, e.g., Taq polymerase.

In one embodiment, the target nucleic acids are amplified in the same reaction vessel (i.e., a multiplex amplification reaction). A variety of multiplex amplification strategies are known in the art and may be used with the methods of the invention. In another embodiment, two or more target nucleic acids are amplified in separate reaction vessels.

If the target sequence is present in a sample, the primers will bind to the sequence and the polymerase will cause the primers to be extended along the target sequence by adding on nucleotides. By raising and lowering the temperature of the reaction mixture, the extended primers will dissociate from the target nucleic acid to form reaction products, excess primers will bind to the target nucleic acid and to the reaction products and the process is repeated, thereby generating amplification products. Cycling parameters can be varied, depending on the length of the amplification products to be extended.

In some embodiments, one or more primer pairs are present in an amplification master mix that further comprises DNA polymerase, dNTPs and PCR buffer prior to contacting with the sample. The sample may be contacted with the primer pair(s) and/or with an amplification master mix to form a reaction-sample mixture.

Amplification of nucleic acids can be detected by any of a number of methods well-known in the art such as gel electrophoresis, column chromatography, hybridization with a probe, sequencing, melting curve analysis, or "real-time" detection. Preferably, the reaction-sample mixture is subjected to real-time PCR conditions under which each of the target nucleic acids present in the sample is amplified and the amplified product(s) are detected and measured.

Accordingly, in some embodiments, at least one primer of each primer pair in the amplification reaction comprises a detectable moiety. The detectable moiety may be on a probe that is attached to the primer, such as with a primer-probe. The probe may be detectably labeled by methods known in the art. Useful labels include, e.g., fluorescent dyes (e.g., Cy5®, Cy3®, FITC, rhodamine, lanthamide phosphors, Texas red, fluorescein amidite (FAM), JOE, a xanthene dye such as Cal Fluor® Red 610 ("CFR610") that fluoresces in the red region of the visible spectrum and can be effectively quenched by a I-BHQ2 dye, Quasar 670®, $^{32}$P, $^{35}$S, $^{3}$H, $^{14}$C, $^{125}$I, $^{131}$I, electron-dense reagents (e.g., gold), enzymes, e.g., as commonly used in an ELISA (e.g., horseradish peroxidase, beta-galactosidase, luciferase, alkaline phosphatase), colorimetric labels (e.g., colloidal gold), magnetic labels (e.g., Dynabeads), biotin, dioxigenin, or haptens and proteins for which antisera or monoclonal antibodies are available. Other labels include ligands or oligonucleotides capable of forming a complex with the corresponding receptor or oligonucleotide complement, respectively. The label can be directly incorporated into the nucleic acid to be detected, or it can be attached to a probe (e.g., an oligonucleotide) or antibody that hybridizes or binds to the nucleic acid to be detected. Thus, following amplification, the various target segments can be identified by using different detectable moieties such as size and/or color. The detectable moiety may be a fluorescent dye. In some embodiments, the different primer pairs are labeled with different distinguishable detectable moieties. Thus, for example, HEX and FAM fluorescent dyes may be present on different primers in the multiplex PCR and associated with the resulting amplicons. In other embodiments, the forward primer is labeled with one detectable moiety, while the reverse primer is labeled with a different detectable moiety, e.g. FAM dye for a forward primer and HEX dye for a reverse primer. Use of different detectable moieties is useful for discriminating between amplified products which are of the same length or are very similar in length. Thus, in certain embodiments, two different fluorescent dyes are used to label different primer-probes used in a single amplification.

In some embodiments, the probes employed are detectably labeled and the detecting is accomplished by detecting the probe label for each amplification product. A quencher may further be associated with the detectable label which prevents detection of the label prior to amplification of the probe's target. TaqMan™ probes are examples of such probes.

TaqMan™ probes (Heid et al., Genome Res, 6:986-994, 1996) use the fluorogenic 5' exonuclease activity of Taq polymerase to measure the amount of target sequences in a sample. TaqMan™ probes are oligonucleotides that contain a donor fluorophore usually at or near the 5' base, and a quenching moiety typically at or near the 3' base. The quencher moiety may be a dye such as TAMRA or may be a non-fluorescent molecule such as 4-(4-dimethylaminophenylazo) benzoic acid (DABCYL). See Tyagi et al., Nature Biotechnology, 16:49-53 (1998). When irradiated, the excited fluorescent donor transfers energy to the nearby quenching moiety by FRET rather than fluorescing. Thus, the close proximity of the donor and quencher prevents emission of donor fluorescence while the probe is intact.

TaqMan™ probes are designed to anneal to an internal region of a PCR product. When the polymerase replicates a template on which a TaqMan™ probe is bound, its 5' exonuclease activity cleaves the probe. This ends the activity of the quencher (no FRET) and the donor fluorophore starts to emit fluorescence which increases in each cycle proportional to the rate of probe cleavage. Accumulation of PCR product is detected by monitoring the increase in fluorescence of the reporter dye (note that primers are not labeled). If the quencher is an acceptor fluorophore, then accumulation of PCR product can be detected by monitoring the decrease in fluorescence of the acceptor fluorophore.

In certain embodiments, the probe and one of the primers of the primer pair may constitute part of the same molecule. This is referred to as a primer-probe (e.g. a Scorpion® primer-probe). In these embodiments, the primer-probe further contains a fluorophore associated with a quencher to reduce background fluorescence. Following PCR extension with such a fluorescent labeled primer-probes, the synthesized target region is attached to the same strand as the probe. Upon denaturation, the probe portion of the primer-probe specifically hybridizes to a part of the newly produced PCR product, physically separating the fluorophore from the quencher, thereby producing a detectable signal. Thus, in some embodiments, one primer of each primer pair may be a primer-probe that comprises a probe sequence element at the 5' end of a primer, wherein the probe element further comprises a fluorophore and a quencher.

The term "fluorophore" as used herein refers to a molecule that absorbs light at a particular wavelength (excitation frequency) and subsequently emits light of a longer wavelength (emission frequency). The term "donor fluorophore" as used herein means a fluorophore that, when in close proximity to a quencher moiety, donates or transfers emission energy to the quencher. As a result of donating energy to the quencher moiety, the donor fluorophore will itself emit less light at a particular emission frequency that it would have in the absence of a closely positioned quencher moiety.

The term "quencher moiety" as used herein means a molecule that, in close proximity to a donor fluorophore, takes up emission energy generated by the donor and either dissipates the energy as heat or emits light of a longer wavelength than the emission wavelength of the donor. In the latter case, the quencher is considered to be an acceptor fluorophore. The quenching moiety can act via proximal (i.e., collisional) quenching or by Forster or fluorescence resonance energy transfer ("FRET"). Quenching by FRET is generally used in TaqMan™ probes while proximal quenching is used in molecular beacon and Scorpion® type probes.

In some embodiments, the probes employed in the disclosed methods comprise or consist of short fluorescently labeled DNA sequences designed to detect sections of DNA sequence with a genetic variation such as those disclosed in French et al. HyBeacon probes: a new tool for DNA sequence detection and allele discrimination, Mol Cell Probes, 2001 December; 15(6):363-74, incorporated by reference herein in its entirety. The central location of the fluorescent molecule within this type of probe provides certain advantages over probes that have signaling chemistry at the end of the DNA probe. HyBeacons® are an example of this type of probe.

In some embodiments, melting curve analysis may be used to detect an amplification product. Melting curve analysis involves determining the melting temperature of nucleic acid amplicon by exposing the amplicon to a temperature gradient and observing a detectable signal from a fluorophore. Melting curve analysis is based on the fact that a nucleic acid sequence melts at a characteristic temperature called the melting temperature (Tm), which is defined as the temperature at which half of the DNA duplexes have separated into single strands. The melting temperature of a DNA depends primarily upon its nucleotide composition. Thus, DNA molecules rich in G and C nucleotides have a higher Tm than those having an abundance of A and T nucleotides.

Where a fluorescent dye is used to determine the melting temperature of a nucleic acid in the method, the fluorescent dye may emit a signal that can be distinguished from a signal emitted by any other of the different fluorescent dyes that are used to label the oligonucleotides. In some embodiments, the fluorescent dye for determining the melting temperature of a nucleic acid may be excited by different wavelength energy than any other of the different fluorescent dyes that are used to label the oligonucleotides. In some embodiments, the second fluorescent dye for determining the melting temperature of the detected nucleic acid is an intercalating agent. Suitable intercalating agents may include, but are not limited to SYBR® Green 1 dye, SYBR® dyes, Pico Green, SYTO dyes, SYTOX dyes, ethidium bromide, ethidium homodimer-1, ethidium homodimer-2, ethidium derivatives, acridine, acridine orange, acridine derivatives, ethidium-acridine heterodimer, ethidium monoazide, propidium iodide, cyanine monomers, 7-aminoactinomycin D, YOYO-1, TOTO-1, YOYO-3, TOTO-3, POPO-1, BOBO-1, POPO-3, BOBO-3, LOLO-1, JOJO-1, cyanine dimers, YO—PRO-1, TO-PRO-1, YO—PRO-3, TO-PRO-3, TO-PRO-5, PO—PRO-1, BO—PRO-1, PO—PRO-3, BO—PRO-3, LO-PRO-1, JO-PRO-1, and mixture thereof. In suitable embodiments, the selected intercalating agent is SYBR® Green 1 dye. By detecting the temperature at which the fluorescence signal is lost, the melting temperature can be determined.

Instrumentation suitable for real time monitoring of PCR reactions is available for use in quantitative PCR methods (ABI Prism 7700, Applied Biosystems Division, Perkin Elmer, Fosters City, Calif., USA; LightCycler®, Roche Molecular Biochemicals, Indianapolis, Ind., USA). Other real time PCR detection systems are known to those of ordinary skill in the art. Real time detection on the instrument monitors fluorescence and calculates the measure of reporter signal, or Rn value, during each PCR cycle. The threshold cycle, or Ct value, is the cycle at which fluorescence intersects the threshold value. The threshold value is determined by the sequence detection system software or manually. The Ct value may be correlated to the amount of initial template nucleic acid in the reaction. The copy number of telomere repeats or target nucleic acid may be determined by comparative quantitative real time PCR. Use of the reference nucleic acids disclosed herein allows quantitation of the copy number of target nucleic acids in a sample.

The method of the present invention is useful in a variety of applications. Real-time qPCR-based telomere length assays provide a reliable and high-throughput method for studying telomeres. The primers reported here make this assay possible in a broad range of vertebrate species. The multiple reference primers reported here provide the opportunity to assess the variability introduced by the reference primers themselves. For the study of new species, it is advisable to first test all five UCE primer pairs on at least ten individuals and performing a stability analysis to find the best two primer pairs. Compared to a single reference primer pair, using the average quantity from two reference primer pairs for relative telomere length measurement has the advantage of averaging out other sources of qPCR noise. While three or more reference primers could be used if warranted, this would require sufficient access to DNA and more reagents.

The ability to determine relative telomere length in any vertebrate species creates new opportunities in basic and applied research. For example, telomere length measurements can be used for monitoring the health and aging of organisms. Telomere lengths have even been considered a proxy for fitness because telomere lengths and shortening rates have been shown to predict lifespan and reproductive success in some species. Telomere lengths in indicator species in different environments may allow identification of important ecosystems disturbances, including those caused by humans. The ability to study multiple species simultaneously opens up questions about how telomere lengths change during long-term predator pray cycles or other ecological interactions. The ability to study telomere length dynamics in diverse taxa allows for a better understanding of aging across the tree of life and from an evolutionary perspective.

In addition to telomere length measurements, the reference primers reported here can also be used in other studies that require quantification of genomic DNA. For example, copy number variation (CNV) within populations represents a large component of genetic diversity that affects normal and disease phenotypes. The reference primers presented here may facilitate a more widespread evaluation of copy number variation in vertebrates, especially because the multiple UCE primers can be used to cross validate the non-variable nature of the reference primers in different genomes.

Telomere lengths may be determined for all chordates, in a preferred embodiment, telomere lengths are determined for vertebrates, including without limitation, amphibians, birds, and mammals, for example rodents, ungulates, and primates, including humans.

In one aspect, the average telomere length or mean telomere length is measured for a single cell, more preferably for a population of cells. A change in telomere length is an increase or decrease in telomere length, in particular an increase or decrease in the average telomere length. The change may be relative to a particular time point, i.e., telomere length of an organism at time point 1 as compared to telomere length at some later time point 2. A change or difference in telomere length may also be compared as against the average or mean telomere length of a particular cell population or organismal population. In certain embodiments, change in telomere length is measured against a population existing at different time periods.

Samples for measuring telomeres are made using methods well known in the art. The telomere containing samples may be obtained from any tissue of any organism, including tissues of blood, brain, bone marrow, lymph, liver spleen, breast, and other tissues, including those obtained from biopsy samples. Tissue and cells may be frozen or intact. The samples may also comprise bodily fluids, such as saliva, urine, feces, cerebrospinal fluid, semen, etc.

The samples containing telomere and target nucleic acids may be prepared using well-known techniques. For instance, the sample may be treated using detergents, sonication, electroporation, denaturants, etc., to disrupt the cells. The target nucleic acids may be purified as needed. Components of the reaction may be added simultaneously, or sequentially, in any order. In addition, a variety of agents may be added to the reaction to facilitate optimal hybridization, amplification, and detection. These include salts, buffers, neutral proteins, detergents, etc. Other agents may be added to improve efficiency of the reaction, such as protease inhibitors, nuclease inhibitors, anti-microbial agents, etc., depending on the sample preparation methods and purity of the target nucleic acid.

In accordance with the present invention, oligonucleotide primers and probes are used in the methods described herein to amplify and detect one or more target reference nucleic acid sequences. In addition, primers are also used to amplify target nucleic acids such as a repetitive unit. In one embodiment, the method involves employing primer pairs specifically directed to the telomere.

As used herein, a "repetitive unit", "repeat unit", "repetitive element" is meant a minimal nucleotide sequence which is reiterated or repeated in the repetitive region, such as a telomere repeat sequence. In the present invention, the repetitive unit for amplification may comprise repetitive units of 1 or more nucleotides, more preferably repetitive units between 3 and 100 nucleotides, and most preferably repetitive units between 4 and 30 nucleotides. In general, these repetitive units are arranged in tandem fashion, although there may be non-repetitive nucleotides present between the repetitive units. By a "plurality" of repetitive elements herein is meant at least two or more repetitive units in the repetitive region. The number of repetitive units amplified for each set of primers will depend on the length of the primer and the nucleotide length of the repetitive unit. As will be appreciated by those skilled in the art, primer sequences and primer lengths may be chosen based on stability and specificity of the primer for the repetitive units.

Generally, the primers for direct amplification of telomere repeats comprises a first primer which hybridizes to a first single strand of the target nucleic acid and a second primer which hybridizes to a second single strand of the target nucleic acid, where the first and second strands are substantially complementary. The primers are capable of primer extension by polymerase when hybridized to their respective strands. That is, the primers hybridized to the target nucleic acid have their 3' terminal nucleotide residues complementary to the nucleotide residue on the target nucleic acid such that the primers are extendable by polymerase. The selected primers are complementary to repetitive units of the repetitive region. In one aspect, at least one nucleotide residue of at least one of the primers is altered to produce mismatches with a nucleotide residue of at least one repetitive unit to which the primer hybridizes, wherein the altered nucleotide residue also produces a mismatch with the 3' terminal nucleotide residue of the other primer when the primers hybridize to each other. The inclusion of a mismatch prevents or limits primer extension of primer-primer hybrids.

Exemplary primer and labeled primer-probe sequences for amplifying and detecting a telomere repeat include:

```
Forward
                                  (SEQ ID NO: 11)
5'-CGGTTTGTTTGGGTTTGGGTTTGGGTTTGGGTTTGGGTT-3'
and Reverse
                                  (SEQ ID NO: 12)
5'-CAGCCGAAAGGCCCTTGGCAGGAGGGCTGCTGGTGGTCTACC

CTT-3'.
```

Kits comprising the reference oligonucleotides which may be primers or primer-probes for performing amplifications as described herein also are provided by the present invention. In some embodiments, a kit comprises one or more primer pairs selected from SEQ ID NOs: 1 and 2, SEQ ID NOs: 3 and 4, SEQ ID NOs: 5 and 6, SEQ ID NOs: 7 and 8, or SEQ ID NOs: 9 and 10. The kit may comprise one, two, three, four, or all five of the primer pairs. A kit of the present invention may further include oligonucleotides that may be used as primers or probes to determine the length of a repetitive region, including a telomere.

The kit additionally may comprise instructions such as printed or electronic instructions for using the oligonucleotides in an assay. In some embodiments, the kit comprises instructions for analyzing a sample to the determine the length of a repetitive region, determine telomere length, or determine copy number variation of a target sequence. In some embodiments, a kit comprises an amplification reaction mixture or an amplification master mix. Reagents included in the kit may be contained in one or more containers, such as a vial. Reagents necessary for amplification and detection of targets may be formulated as an all-in-one amplification master mix, which may be provided as single reaction aliquots in a kit.

EXAMPLES

Example 1: Assay Development

Figure 1B:
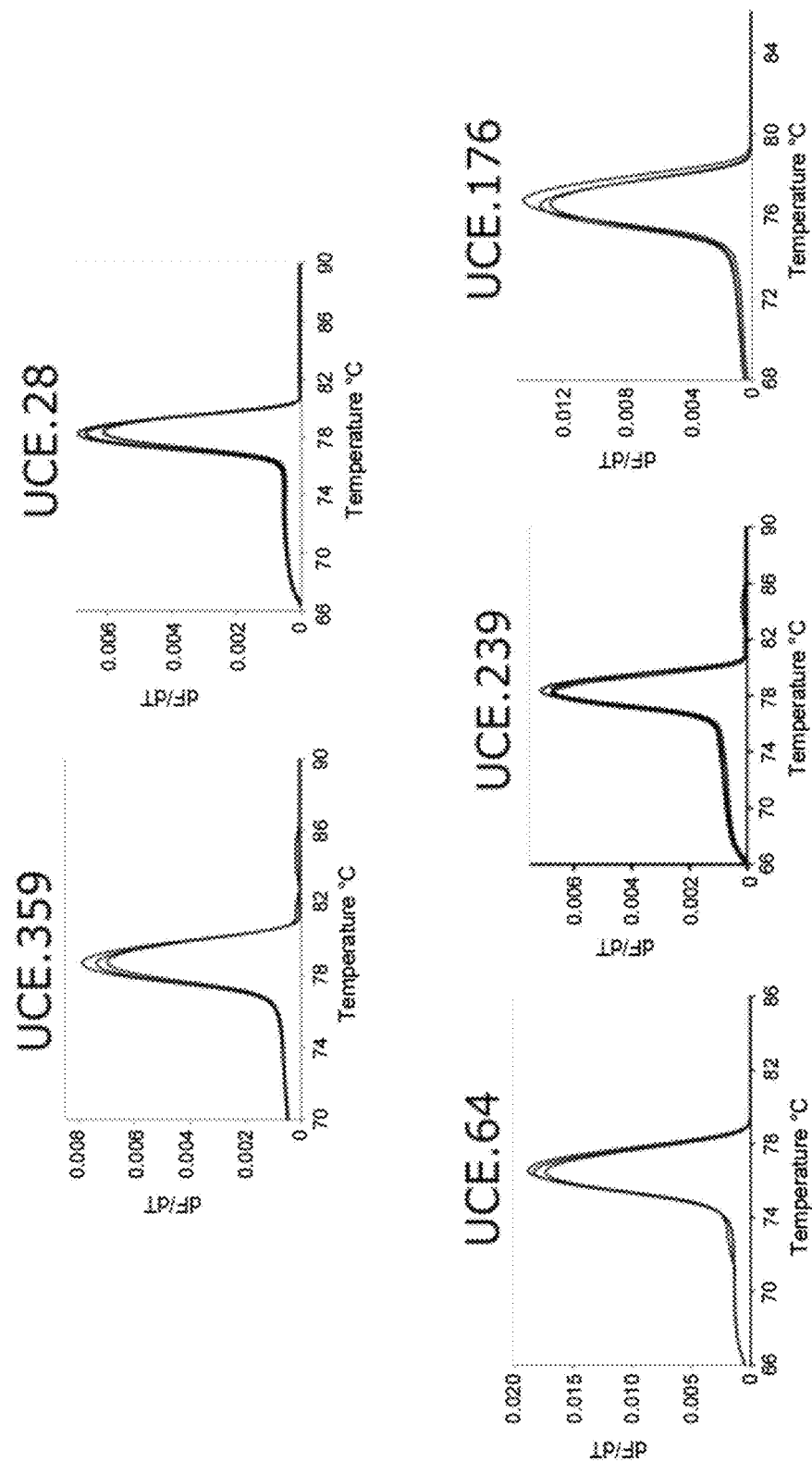

We set out to develop primer pairs to several UCEs to enable cross validation (FIG. 1A). We chose several UCEs from UCbase 2.0 and designed multiple primer pairs for each using a primer design tool (OligoArchitect, Sigma-Aldrich). During design, we limited the product length to 250 bps and designed primers to have a Tm of 60° C. to match the Tm of established telomere-specific primers. We ranked the primer pairs computationally (Beacon Designer) and experimentally tested the top four pairs for each of the UCEs by amplifying mouse DNA in a qPCR reaction. Using melt-curve analysis, we identified primer pairs for five of the UCEs that produced a single-peaked melt curve (FIG. 1B). We determined the amplification efficiency for each of these five UCE primer pairs by amplifying seven serial dilutions of the mouse DNA in triplicate (FIG. 1C). A primer pair for all five UCEs was found that have qPCR efficiencies within the best-practice range of 90-110% and correlations ($R^2$) of the Cq values for replicates greater than or equal to 0.980 (FIG. 1C). The sequences of the chosen UCE primer pairs are shown in Table 1.

TABLE 1

| | Forward Sequence 5'-3' | Reverse Sequence 5'-3' |
|---|---|---|
| UCE.359-F/R | ATCTGAGACTTGTGACAT (SEQ ID NO: 1) | GTGTTAATTGGTAATGACT ATT (SEQ ID NO: 2) |
| UCE.28-F/R | AAATACCACCCAACAGTT T (SEQ ID NO: 3) | AAGCCCTATACAGATGGAT (SEQ ID NO: 4) |
| UCE.64-F/R | GAGTCTCCAATATCATCA GAAGC (SEQ ID NO: 5) | ACACATGCCACGATCAATG (SEQ ID NO: 6) |
| UCE.239-F/R | TCAGATGTTCAGCCTATT (SEQ ID NO: 7) | AATACCATGTTAATTATCC TCAA (SEQ ID NO: 8) |
| UCE.176-F/R | TTTCTACAGTTCTGATTT AGTTGA (SEQ ID NO: 9) | TGTTCCCTGTCGCATTAG (SEQ ID NO: 10) |
| Telomere | CGGTTTGTTTGGGTTTGG GTTTGGGTTTGGGTTTGG GTT (SEQ ID NO: 11) | CAGCCGAAAGGCCCTTGGC AGGAGGGCTGCTGGTGGTC TACCCTT (SEQ ID NO: 12) |

Example 2: Validation Across the Vertebrate Tree of Life

Figure 2A:
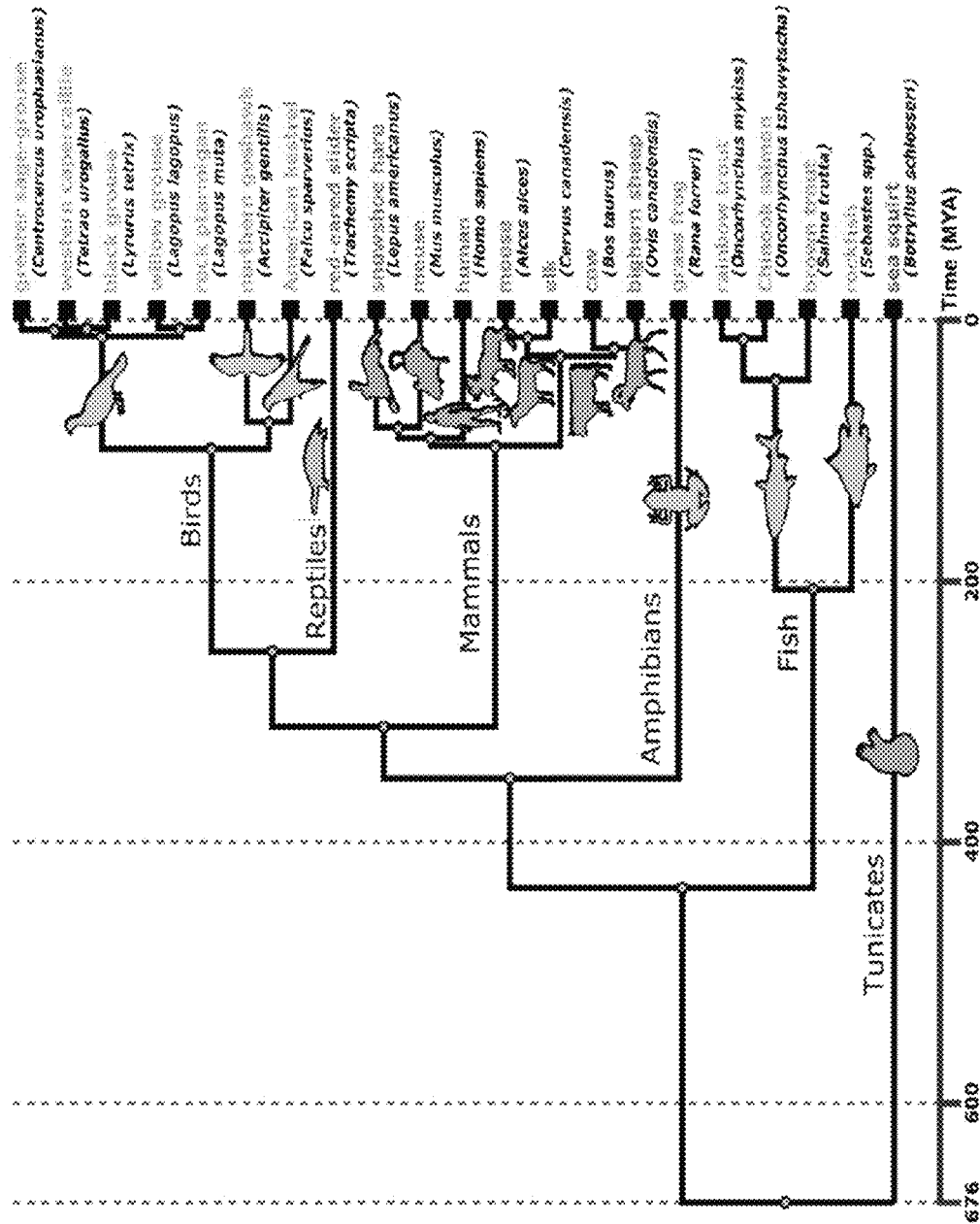
FIGS. 2A-D show validation of UCE reference primers across the vertebrate tree of life.

We next tested our primers across the vertebrate tree of life (FIG. 2A). We collected various tissue types from 19 species for DNA extraction. This generally was isolated from a single individual unless the DNA was of insufficient concentration to complete testing. To test our primers as broadly as possible, we also included a sea squirt, which is amendable to telomere length measurements because basal chordates have the same telomeric repeat sequences as vertebrates. We performed qPCR on each sample in triplicate with all five primer pairs and evaluated the melt-curves. We found that all five primer pairs amplified DNA from every species with a single melt peak. These results indicate that all five primer pairs can amplify the ultraconserved regions in all vertebrates that we tested.

Figure 2B:
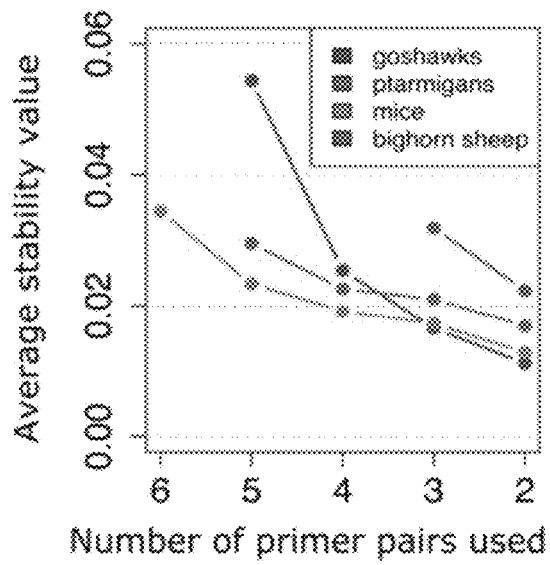
Figure 2C:
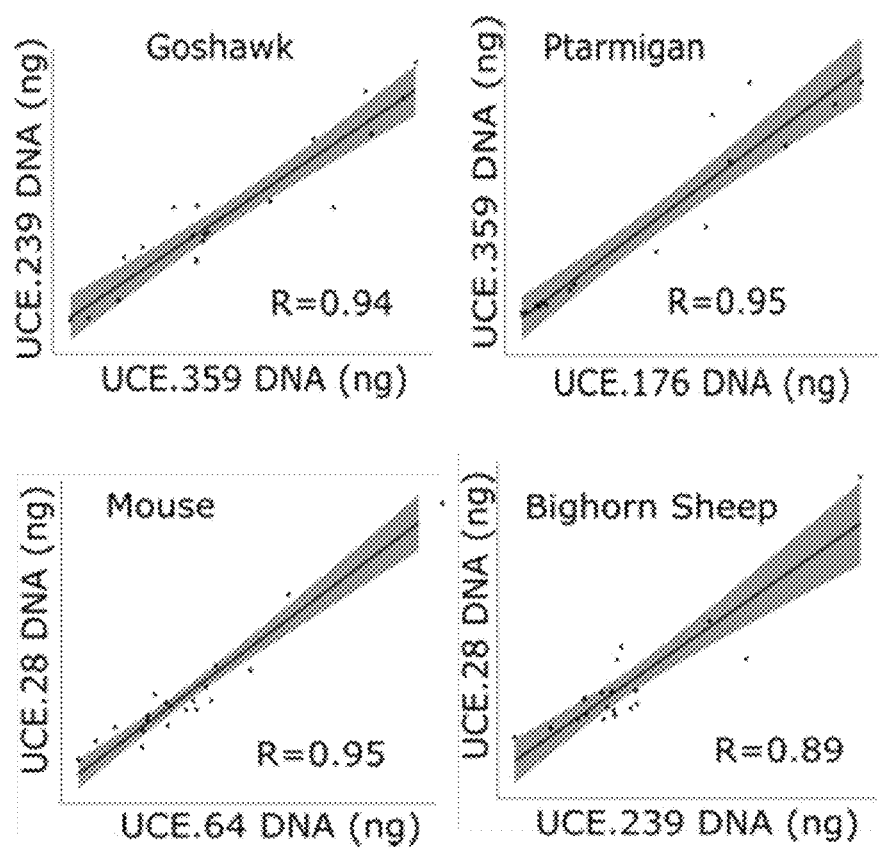

An additional requirement for reference genes used for normalizing telomere length is that they must not vary in copy number among individuals in the population. For example, a duplication of a reference gene in one individual would appear as a halving of their telomere lengths relative to a non-duplicated individual. The amplification of closely related homolog variants could also introduce normalization differences that would have the same effect as copy number variation. The challenge of identifying reference primers with minimal variation between individuals for telomere length measurements is similar to choosing primer pairs for normalizing real-time PCR data for gene expression. We therefore evaluated our primer pairs using an algorithm, geNorm, designed for this purpose. The geNorm algorithm evaluates the cumulative variation among multiple primer pairs and iteratively eliminates primer pairs that contribute the most variation until final primer pairs are chosen. In this approach, stability values are a measurement of the pairwise variation between primers and therefore lower stability values are preferred. Two or more primer pairs are preferred over a single primer pair to reduce random experimental variation. Using the NormqPCR package in R which utilizes the geNorm algorithm, we identified the best combination of UCE primer pairs from DNA extracted from 20 mice (*Mus musculus*), 17 rock ptarmigan (*Lagopus muta*), and 20 northern goshawks (*Accipiter gentilis*), representing both sexes and a range of ages. Samples were amplified by qPCR with each of the five reference primer sets using the same DNA concentration (8 ng) for each reaction. We found that the use of two primer pairs for normalization leads to very low stability values in each of the four species tested (FIG. 2B). Next, we extracted DNA from another mammal (bighorn sheep, *Ovis canadensis*) and tested the top three primer pairs which had been identified in mouse. Using NormqPCR we identified the two primer pairs with the lowest stability values (FIG. 2B). The genomic DNA concentration quantified by these two primer pairs showed high correlation (Pearson), suggesting that neither pair exhibit copy number polymorphisms within the individuals tested (FIG. 2C and FIG. 3). We also tested primer efficiency in these four animals and found that all primers tested fell within the recommended range of 90-110% (Table 2).

TABLE 2

| | UCE.28 | UCE.239 | UCE.64 | UCE.359 | UCE.176 |
|---|---|---|---|---|---|
| Northern Goshawk | 110% | 102% | 98% | 102% | 103% |
| Ptarmigan | 100% | 108% | 103% | 104% | 99% |
| Mouse | 95% | 101% | 101% | 97% | 102% |
| Bighorn Sheep | 102% | 104% | 108% | N/A | N/A |

Figure 2D:
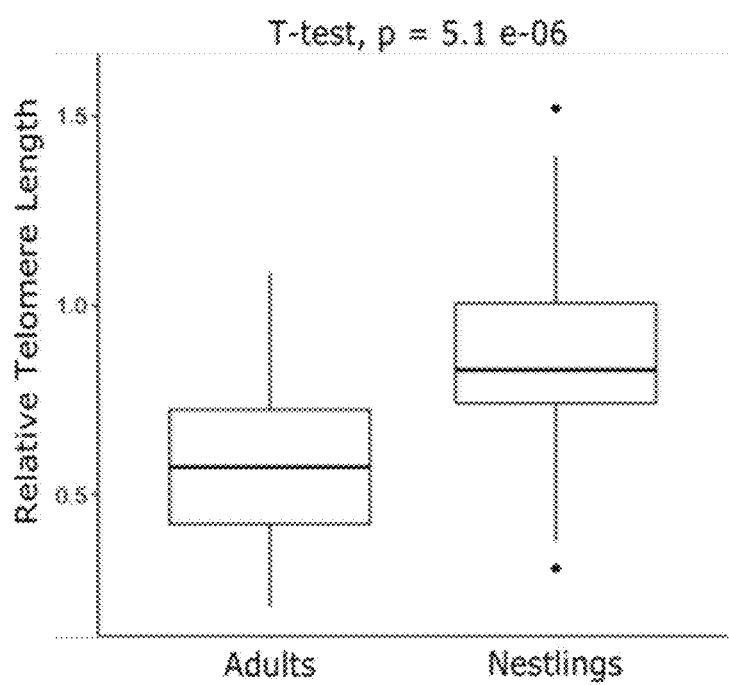
Figure 3A:
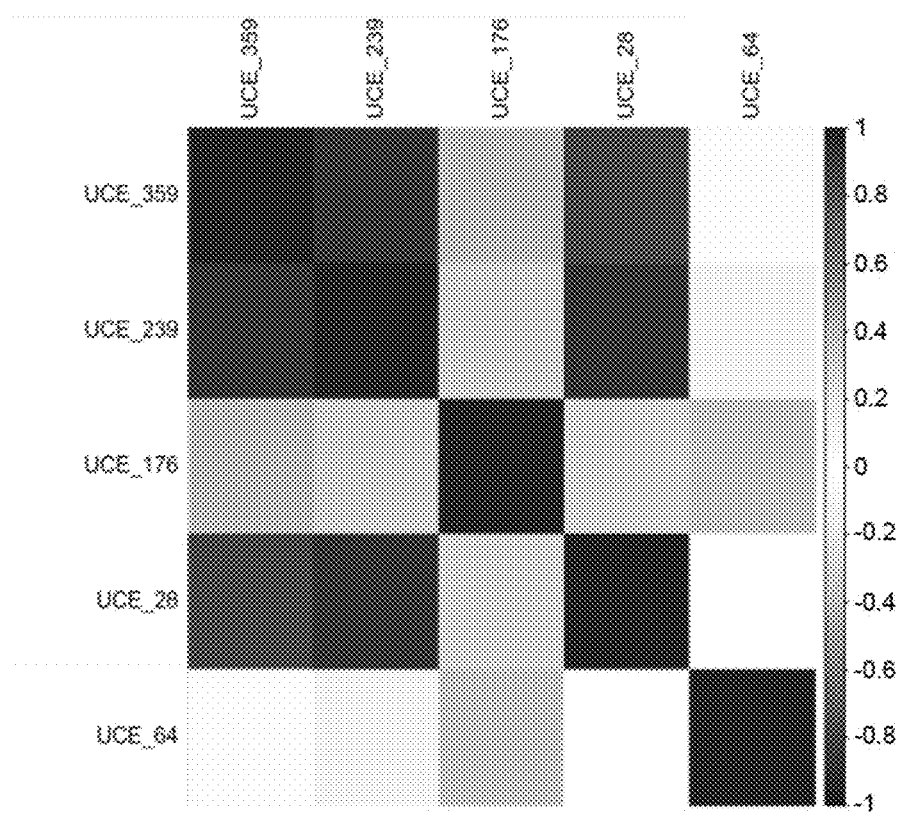
FIGS. 3A-D show Pearson correlation matrixes for UCE primers in four organisms.
Figure 3B:
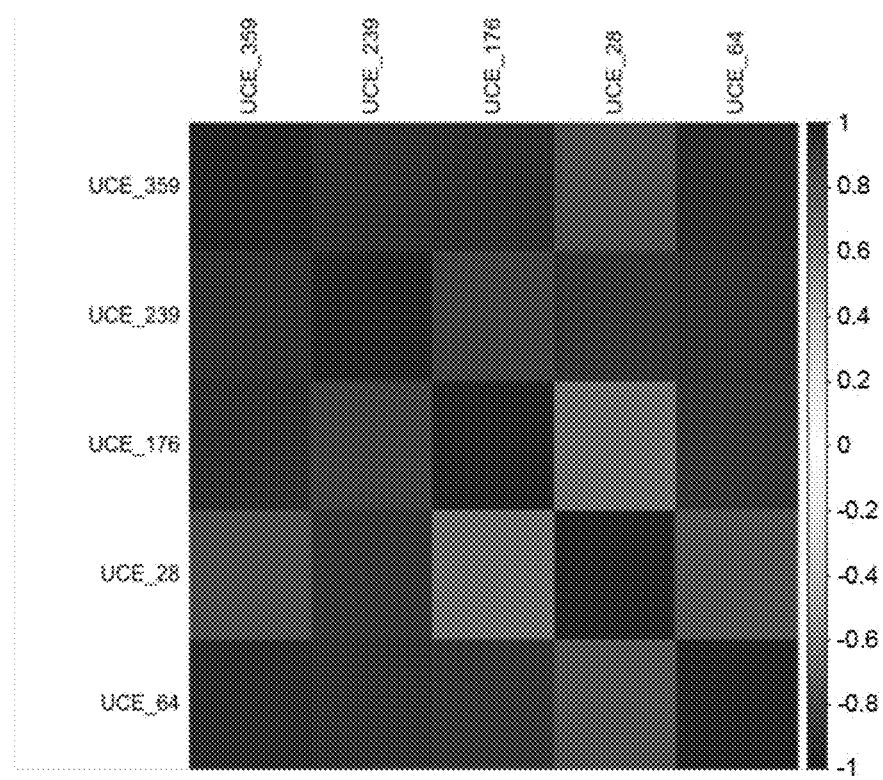
Figure 3C:
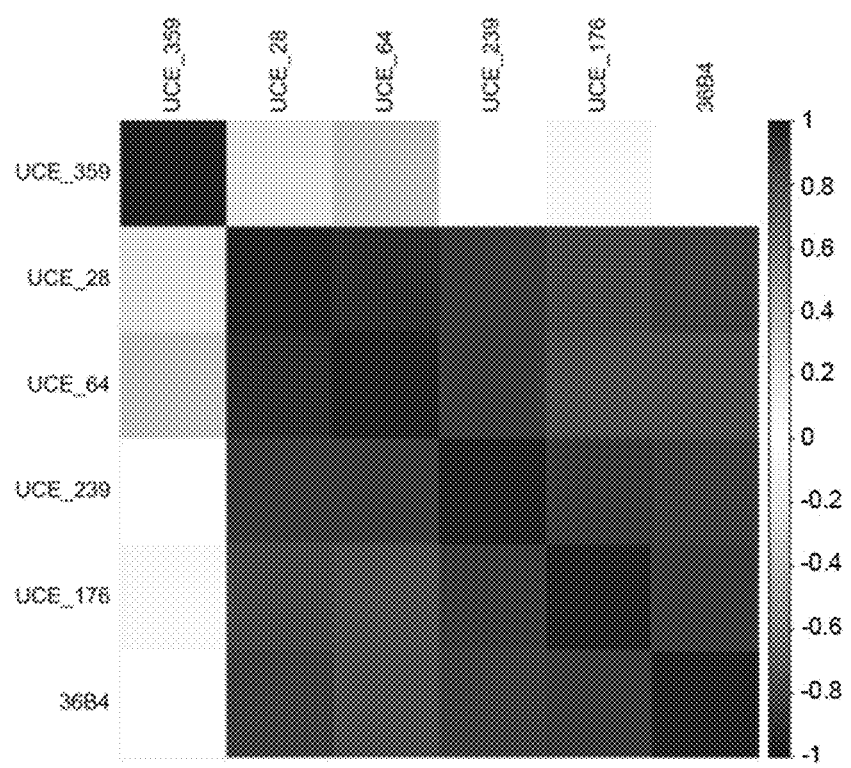
Figure 3D:
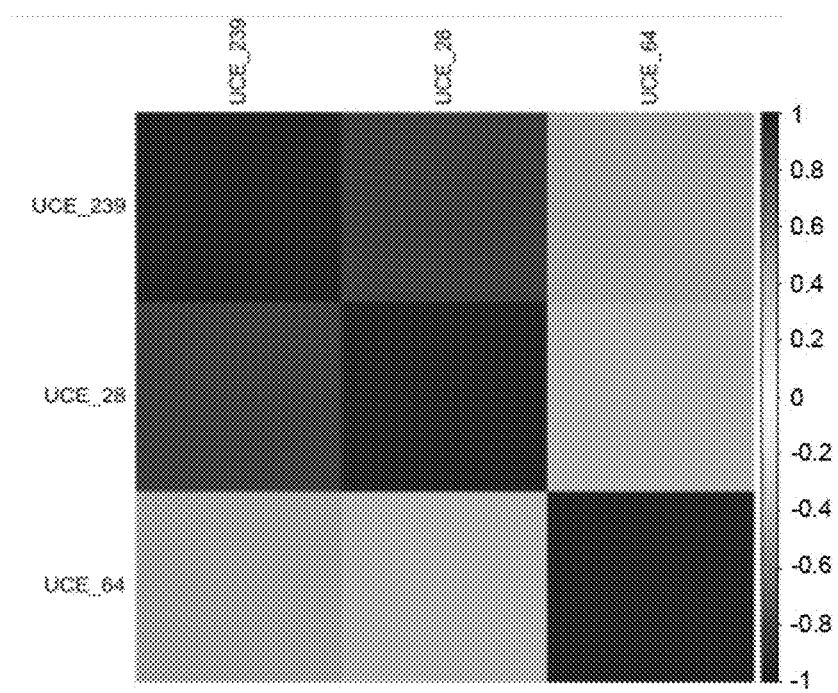
Figure 4:
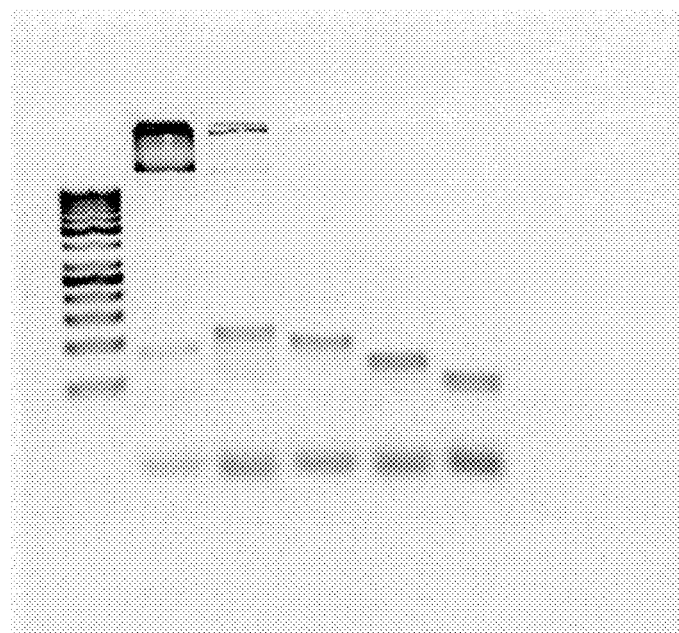
FIG. 4 shows GAPDH PCR variants in American Kestrel. PCR products of multiple sizes created in various American Kestrel samples.

We next set out to determine if the UCE-based assay yields expected relative telomere length measurements in a species where telomere lengths have not been previously measured. We extracted DNA from the blood of 15 adult and 29 nestling American kestrels. We amplified each DNA sample separately with telomere specific primers, UCE.28 and UCE.239 which were chosen because of low stability values and high correlations. Relative telomere length was calculated as the ratio of the telomere amplification product to the average of the UCE amplification products. The results showed that adult American kestrels had a significantly shorter telomere length than nestlings (FIG. 2D). We note that, prior to developing the UCE primers, we had attempted to utilize published GAPDH primers to normalize telomere lengths in the American kestrel. We found that both the published and extensively redesigned and optimized GAPDH primers exhibited unpredictable variation in the size of PCR products between individuals, making this commonly used reference gene unsuitable in this organism (FIG. 4). These results suggest that our primers may even be an improvement for telomere assays in avian species.

Figure 5:
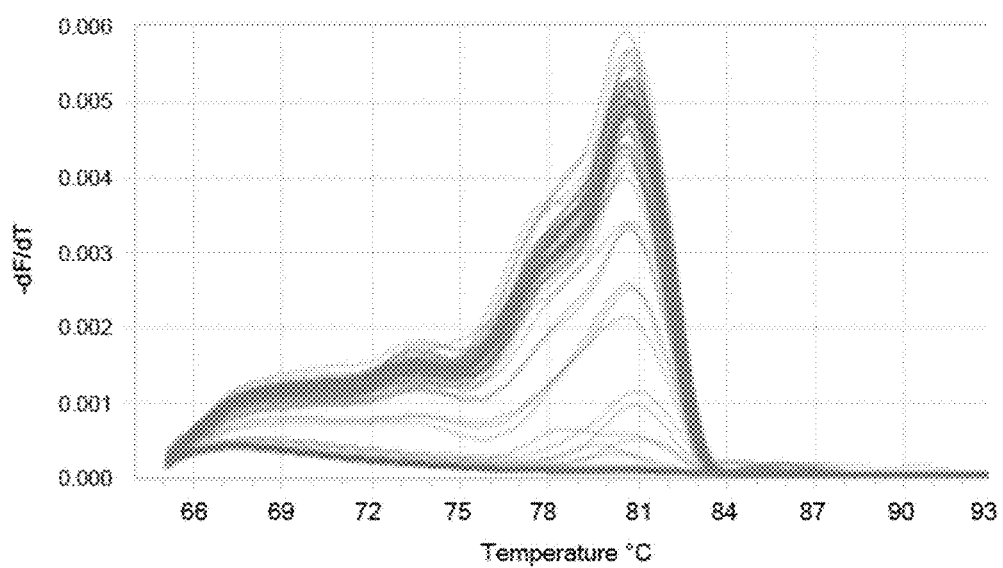
FIG. 5 shows melt curve of frequently utilized 36B4 reference primers used in qPCR-based telomere assays in mice.

We next quantified 20 mouse samples with a reference primer pair previously reported in the literature that was designed for qPCR-based telomere length measurement in mice. The previously reported primers target the acidic ribosomal phosphoprotein PO (36B4) gene and have been used in multiple publications. We used the published thermal cycling profile of the 36B4 primers to determine the PCR efficiency and evaluate the melt peak. The 36B4 primers had a good efficiency (102%) but showed a broad, multi-peaked melt-curve indicating PCR artifacts or non-specific amplification occurred (FIG. 5). When we included the 36B4 primer pair in the NormqPCR stability analysis for mouse, this primer pair was the second eliminated by the geNorm algorithm, indicating that our top UCE primer pairs are an improvement with respect to genomic reference stability values in mice. These results further suggest that our UCE reference primers may be useful even in organisms with established reference primers.

Genomic DNA Extraction

DNA was extracted from blood or tissue samples using the Zymo Quick-DNA Microprep Plus Kit (#D4074) according to the manufacture's protocols for the sample type. Blood samples from Northern goshawk and American kestrel were stored in Queen's lysis buffer (0.01 M Tris, 0.01 M NaCl, 0.01 M EDTA, and 1% n-lauroylsarcosine, pH 7.5) prior to extraction. Human DNA was from a buccal swab. DNA from a red-eared slider was extracted from a shell fragment. DNA from sea squirt was extracted from whole organisms. All other DNA samples were extracted from muscle tissue. All animals were treated in accordance with Boise State University animal care and use policies where applicable. DNA purity was assessed by 260/280 nm absorbance ratio (NanoDrop). DNA was quantified by absorbance at 260 nm and the concentration was normalized to 2 ng/µl in 10 mM Tris-HCl pH 8.5 and 0.1 mM EDTA.

Quantitative PCR

Quantitative PCR (qPCR) was performed using a Roche LC96. For each UCE primer pair, efficiencies were determined using a serial dilution of mouse DNA samples, performed in triplicate. The standard curve was prepared by seven serial dilutions (1:5). All qPCR reactions were carried out in 20 µL volumes containing approximately 8 ng DNA for unknown samples (or 4 µl of varying concentrations of DNA for serial dilutions), 10 µl of 2× Biotium Fast Plus EvaGreen® qPCR Master Mix, 10 pmol each of forward and reverse primers (500 nM final primer concentration) and water up to 20 µl. For both UCE and telomere amplification the two-step thermal cycling profile was 95° C. for 2 min, followed by 40 cycles of 95° C. for 5 s and 55° C. for 30 s, with signal acquisition at the end of the 55° C. step and melt curves generated by increasing temperatures from 72 to 95° C., in 0.5° C. steps, with a 30 s dwell period per step at the end of the thermal cycling. Amplification of kestrel samples were carried out under identical conditions, using the same thermal cycling. Reactions with previously reported primers for 36B4 in mice contained 250 nM final concentration of forward and reverse primers with all other reagents as described above. PCR reactions with the 36B4 primers were thermal cycled for 95° C. for 2 min, followed by 35 cycles of 94° C. for 30 s, 52° C. for 30 s, and 72° C. for 30 s with a final extension for 5 min at 72° C. and signal acquisition at the end of the 72° C. step and melt curves generated by increasing temperatures from 72 to 95° C., in 0.5° C. steps, with a 30 s dwell period per step at the end of the thermal cycling. PCR reactions for GAPDH (Forward 5'-CTAAGCGTGTTATCATCT-3' (SEQ ID NO: 13), Reverse 5'-ACTTGTCATACTTGTCAT-3' (SEQ ID NO: 14)) were thermal cycled at 95° C. for 2 min, followed by 40 cycles of 95° C. for 5 s and 55° C. for 30 s, with signal acquisition at the end of the 55° C. step.

The Cq values determined for technical replicates were averaged and any sample with a quantification cycle (Cq) standard deviation of greater than 0.5 between triplicates or with Cq values outside of the standard curve were repeated. Concentrations (ng) of telomere repeats and UCEs were determined using an external standard curve approach and Roche LightCycler software (release 4.0) for Absolute Quantification auto-analysis with the second derivative maximum method (proprietary). The efficiencies of each primer pair were determined from the slope of the standard curves using Roche LightCycler software where $E = 10^{[-1/slope]}$. Optimal efficiency (100%) is defined as a slope of 3.32. The correlation coefficients ($R^2$) were determined from the replicates of the dilution series.

Data Analysis

For the 21 species in which we tested our primers, we constructed a phylogenetic tree based on the tree-of-life and its evolutionary timescale. We loaded the 21 species into TimeTree (timetree.org) and generated a phylogenetic tree that showed the 21 extant species and ancestral progenitors. Primer pairs were assessed for their effect on stability values computationally (geNorm) in four of the 21 vertebrates. The same genomic DNA samples from multiple individuals were amplified with 3-5 UCE primer pairs, and the Cq values were used to sequentially eliminate the least stable primer pair. The two most stable UCE primer pairs were then used to generate DNA concentrations (ng) from a standard curve and these concentrations were graphed on a scatter plot with Pearson correlations and trend lines reported. Genomic DNA from the organism of interest which had the highest concentration, measured by UV absorbance, was used for the standard curve. To calculate relative telomere lengths in adult and nestling kestrels, the telomere concentration (T) was divided by the average concentration of two UCE genes ($UCE_{ave}$) to yield $T/UCE_{ave}$.

What is claimed is:

1. A method for determining telomere length in a genomic DNA sample, the method comprising:
   amplifying the genomic DNA with a first oligonucleotide pair specific for a telomere repeat and a second oligonucleotide pair specific for a reference sequence,
   wherein the second oligonucleotide pair comprises SEQ ID NOs: 1 and 2, SEQ ID NOs: 3 and 4, SEQ ID NOs: 5 and 6, SEQ ID NOs: 7 and 8, or SEQ ID NOs: 9 and 10, or a sequence having at least 80% sequence identity thereto.

2. The method of claim 1, wherein the first oligonucleotide pair comprises SEQ ID NOs: 11 and 12, or a portion or conservatively modified variant thereof that is sufficiently complementary to hybridize to the telomere repeat.

3. The method of claim 1, wherein the sample is from a chordate.

4. The method of claim 1, wherein the sample is from a mammal, fish, bird, reptile, or amphibian.

5. The method of claim 1, wherein the sample is from a human.

6. The method of claim 1, wherein the amplifying is performed using quantitative real time PCR.

7. The method of claim 1, wherein the amount of amplification product produced by the first oligonucleotide pair is normalized to the amount of amplification product produced by the second oligonucleotide pair to determine the telomere length.

8. The method of claim 1, wherein the oligonucleotide pairs are contained together in an amplification master mix further comprising DNA polymerase, dNTPs, and PCR buffer prior to amplifying.

9. The method of claim 1, wherein at least one oligonucleotide of each oligonucleotide pair is associated with a detectable label.

10. The method of claim 1, wherein the method comprises amplifying the genomic DNA with two or more reference oligonucleotide pairs selected from SEQ ID NOs: 1 and 2, SEQ ID NOs: 3 and 4, SEQ ID NOs: 5 and 6, SEQ ID NOs: 7 and 8, and SEQ ID NOs: 9 and 10, or a sequence having at least 80% sequence identity thereto.

11. A method for predicting lifespan or reproductive success of an organism, the method comprising:
   obtaining a biological sample comprising genomic DNA from the organism; and
   determining telomere length by amplifying the genomic DNA with a first oligonucleotide pair specific for a telomere repeat and a second oligonucleotide pair specific for a reference sequence,
   wherein the second oligonucleotide pair comprises SEQ ID NOs: 1 and 2, SEQ ID NOs: 3 and 4, SEQ ID NOs: 5 and 6, SEQ ID NOs: 7 and 8, or SEQ ID NOs: 9 and 10, or a sequence having at least 80% sequence identity thereto, wherein telomere shortening indicates reduced lifespan or reproductive success.

12. A method of determining the age of a cell, the method comprising:
   obtaining genomic DNA from the cell;
   determining telomere length by amplifying the genomic DNA with a first oligonucleotide pair specific for a telomere repeat and a second oligonucleotide pair specific for a reference sequence,
   wherein the second oligonucleotide pair comprises SEQ ID NOs: 1 and 2, SEQ ID NOs: 3 and 4, SEQ ID NOs: 5 and 6, SEQ ID NOs: 7 and 8, or SEQ ID NOs: 9 and 10, or a sequence having at least 80% sequence identity thereto; and
   estimating the age of a cell based on the telomere length.

* * * * *